United States Patent
Balschat et al.

(10) Patent No.: US 9,782,528 B2
(45) Date of Patent: Oct. 10, 2017

(54) CONCENTRATE CONTAINER HAVING SUPPORTING ELEMENTS

(71) Applicant: Fresenius Medical Care Deutschland GmbH, Bad Homburg (DE)

(72) Inventors: Klaus Balschat, Schwebheim (DE); Alfred Gagel, Litzendorf (DE); Dirk Huemmer, Hirschfeld (DE); Peter Kloeffel, Nuedlingen (DE); Olaf Nicholas, Kitzingen (DE); Tilman Staeblein, Wuerzburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 13/908,229

(22) Filed: Jun. 3, 2013

(65) Prior Publication Data
US 2013/0333795 A1 Dec. 19, 2013

Related U.S. Application Data

(60) Provisional application No. 61/656,309, filed on Jun. 6, 2012.

(30) Foreign Application Priority Data

Jun. 6, 2012 (DE) .......................... 10 2012 011 250

(51) Int. Cl.
*A61M 1/14* (2006.01)
*B65D 75/00* (2006.01)
(Continued)

(52) U.S. Cl.
CPC .............. *A61M 1/14* (2013.01); *A61M 1/167* (2014.02); *A61M 1/1656* (2013.01);
(Continued)

(58) Field of Classification Search
CPC .. B65D 35/14; B65D 81/3272; B65D 75/008; B65D 81/3261; A61M 1/1668
See application file for complete search history.

(56) References Cited

U.S. PATENT DOCUMENTS 2,865,768 A * 12/1958 Barnes ............... B65D 81/3407
229/125.37
3,508,374 A * 4/1970 Bertoglio ................ B29C 65/02
383/104

(Continued)

FOREIGN PATENT DOCUMENTS

| CN | 1905853 | 1/2007 |
|---|---|---|
| CN | 101184672 | 5/2008 |

(Continued)

*Primary Examiner* — Krishnan S Menon
*Assistant Examiner* — Waqaas Ali
(74) *Attorney, Agent, or Firm* — Jacobson Holman, PLLC.

(57) ABSTRACT

A container for dialysis concentrates, in particular acidic dry concentrates, has integral supporting elements. When these dry concentrates are dissolved directly by a dialysis machine to form liquid concentrates, the container must provide a volume of 4-12 liters. To impart the required stability to the container, the container includes the integral supporting elements, which manifest their supporting function only when the container is used on the dialysis machine.

10 Claims, 5 Drawing Sheets

(51) Int. Cl.
*B65D 33/02* (2006.01)
*A61M 1/16* (2006.01)
(52) U.S. Cl.
CPC ........... *A61M 1/1668* (2014.02); *B65D 33/02* (2013.01); *B65D 75/008* (2013.01)

(56) References Cited

U.S. PATENT DOCUMENTS

| | | | | |
|---|---|---|---|---|
| 3,980,225 | A * | 9/1976 | Kan | ........................ B31B 19/36 383/104 |
| 4,810,844 | A * | 3/1989 | Anderson | .............. B65D 31/10 219/727 |
| 4,950,859 | A * | 8/1990 | Anderson | .......... B65D 81/3461 219/727 |
| 4,954,124 | A * | 9/1990 | Erickson | ............. B29C 65/7437 156/308.4 |
| 6,375,037 | B1 * | 4/2002 | Bell | ..................... B65D 75/008 206/439 |
| 6,648,201 | B1 * | 11/2003 | Marinaro et al. | ............... 227/95 |
| 7,452,132 | B2 * | 11/2008 | Tang | .................. B65D 33/2508 383/100 |
| 2002/0076471 | A1 | 6/2002 | Olsson | |
| 2003/0015549 | A1 * | 1/2003 | Yoshida | ........................ 222/103 |
| 2003/0103694 | A1 * | 6/2003 | Cook | ..................... B65D 31/04 383/113 |
| 2006/0048132 | A1 | 3/2006 | Chen et al. | |
| 2007/0145137 | A1 | 6/2007 | Mrowiec | |
| 2008/0149701 | A1 | 6/2008 | Lane | |
| 2008/0272146 | A1 * | 11/2008 | Kaczmarek | .......... B65D 75/525 222/105 |
| 2008/2472146 | | 11/2008 | Kaczmarek | |
| 2009/0297741 | A1 | 12/2009 | Oshita et al. | |
| 2009/0320684 | A1 * | 12/2009 | Weaver et al. | ................... 96/12 |
| 2010/0225653 | A1 | 9/2010 | Sao et al. | |
| 2010/0269909 | A1 * | 10/2010 | Brandl | ................ A61M 1/1656 137/1 |
| 2011/0166968 | A1 | 7/2011 | Houng et al. | |
| 2012/0128267 | A1 | 5/2012 | Dugan et al. | |
| 2013/0011085 | A1 | 1/2013 | Umenaka | |

FOREIGN PATENT DOCUMENTS

| | | |
|---|---|---|
| CN | 101443056 | 5/2009 |
| CN | 101495163 | 7/2009 |
| DE | 10 2011 106 248 | 1/2010 |
| EP | 1 344 550 | 9/2003 |
| EP | 1 757 222 | 2/2007 |
| GB | 2 311 753 | 10/1997 |
| JP | 2003026233 A * | 1/2003 |
| WO | WO 96/01775 | 1/1996 |
| WO | WO 2005/004783 | 1/2005 |
| WO | WO 2005/120972 | 12/2005 |
| WO | WO 2007/144427 | 12/2007 |
| WO | WO 2011/115270 | 9/2011 |

\* cited by examiner

CONCENTRATE CONTAINER HAVING SUPPORTING ELEMENTS

CROSS-REFERENCE TO RELATED APPLICATION

This application claims the benefit of priority to U.S. Provisional Application No. 61/656,309.

BACKGROUND OF THE INVENTION

1. Field of Invention

The invention relates to a container for preparing dialysis concentrate having integrated supporting elements.

2. Description of the Prior Art

The documents EP 1 344 550 and DE 10 2011 106 248.7 describe containers for preparing concentrates for dialysis. Containers having supporting elements are known from WO 2005/120972, for example.

In treatment of renal failure by hemodialysis, approximately 180 liters of dialysis solution are required per treatment. To minimize the cost of shipping and storage of these products, they are usually shipped in the form of concentrates, with the basic and the acidic concentrates being prepared separately for reasons of stability.

The basic concentrate is usually supplied as a dry concentrate consisting of pure sodium bicarbonate. A saturated solution is prepared from this by the dialysis machine in a flow-through process, which means that during the procedure, there is always a certain amount of undissolved salt present in the container. Water is supplied continuously and the saturated solution is removed continuously. The volume of the container for the basic concentrate thus corresponds approximately to the volume of the salt required for a treatment (approximately 0.5-1 liters).

The acidic concentrate is usually supplied as a liquid concentrate. It consists mainly of table salt and contains additional electrolytes such as magnesium, calcium and potassium chloride, the acid and possibly other additives, e.g., glucose, in much smaller amounts. If the acidic concentrate is supplied as a dry concentrate, it cannot be prepared in a continuous process like the basic concentrate. The concentrations of the components such as potassium and calcium, which are present only in very small amounts, must be maintained accurately to obtain a dialysis solution that is safe for the patient. The entire dry concentrate in the container must be dissolved before being diluted to form the dialysis fluid. In order for this to be possible, the container for the acidic concentrate must provide a much larger volume (approximately 4-12 liters) than the container for the basic concentrate. For shipping and storage, the container should only claim the smallest possible volume. A bag that can be folded to the smallest possible size and then unfolds when filled with a fluid is especially suitable for this purpose.

If the concentrate is present in dry form, liquid must be supplied to the container by the dialysis machine to dissolve the dry concentrate and then removed again after preparing the liquid concentrate. The container must therefore be attached to the dialysis machine with a connector in a fluid-tight connection. The containers are attached to the connectors of the dialysis machine via a connecting means. If the containers have a larger volume and thus also have a larger weight, this results in a tensile stress on the corresponding connectors.

The object of the present invention is to make available flexible containers for concentrates, which are as small and as lightweight as possible for shipping and storage. During use, they should provide a larger volume and they should have a great stability and the tensile stress on the dialysis machine should be largely prevented.

According to the teaching of the present invention, this object is achieved by a container, a use of the container, a dialysis machine, and a method as described herein. Advantageous features of the aforementioned emobodiments are also described herein.

SUMMARY OF THE INVENTION

The invention relates to a container for a concentrate suitable for preparing a dialysis solution. This container has a connecting means, by means of which the container can be connected to a dialysis machine or to a preparation unit for liquid concentrates. Two fluid connections between the dialysis machine and the container are established by the connecting means. The supply of a fluid, preferably water or the supply of a gas, preferably air, is possible through one of these fluid connections each. Simultaneous supply of fluid and gas is also possible. In a preferred embodiment, this fluid connection also serves to remove the concentrate from the container. The second fluid connection may be used to vent the container. This fluid connection may in turn contain a non-return valve. This valve may open into the container on reaching a certain inside pressure. This prevents an excessively high pressure in the container. Furthermore, the container has integrated supporting elements. These supporting elements are designed to increase the volume and the weight of the container as little as possible before use of the container on a dialysis machine or a preparation unit. Therefore, they hardly increase the cost of shipping and storage of the product. Only in the supply of fluid and/or a gas into the container do the elements characterize their supporting function. The supporting element may be an air cushion here. This air cushion is filled by the supply of air. Due to the selection of the valve in the vent line, it is possible to build up a pressure in the container, which can be used to fill the air cushion.

The air cushion may form an outer bag around the concentrate-filled inner bag, which largely surrounds the latter and thereby stabilizes it. The air cushion may also consist of multiple compartments. The outer bag may be designed so that the container is self-standing after the air cushion is filled. In a preferred embodiment, the inner bag and the outer bag are connected via a non-return valve. Then the outer bag can be filled by supplying gas into the inner bag through the fluid line to the dialysis machine. The gas is sent to the inner container via an insertion means and passes through the non-return valve into the outer bag. Once the outer bag has been filled, excess gas can be removed through a venting means in the inner bag.

Alternatively, the outer bag may also be equipped with a separate access through which a gas can be supplied.

In an alternative embodiment, the vent means may be embodied as a pleated foot connected to the container. This foot unfolds when the container is filled with a liquid and/or air and thereby influencing its support function. In a preferred embodiment, the foot is also designed so that the bag itself is self-standing.

In a preferred embodiment, the concentrate present in the container is dry concentrate. If the dry concentrate is the acidic concentrate, as described above, then the entire concentrate must be dissolved as described above before it can be used to prepare a dialysis solution. The amount of salt in the container must be sufficient to perform at least one dialysis treatment. Furthermore, the dilution ratios in the machine for preparing the dialysis solution are fixed, which is why the container must provide a certain volume. Then after the container has been filled with a liquid, preferably water, to its target concentration, it has a volume between 4 and 15 liters.

A container for dry concentrate must also have a region of wall areas facing one another, forming a valley-shaped region or a recess between them, such that the dry concentrate is also present at least in the valley-shaped region and/or in the recess in the operating position of the container. In this region, the insertion means for the fluid, preferably water and/or gas, preferably air, then also protrudes into this region. Thus the dissolution of the concentrate is optimized, as described in DE 10 2011 106 248.7. However, conventional containers such as stand-up bags cannot be used for this purpose. Special supporting elements according to the invention are then especially advantageous.

The invention also relates to the use of a container according to the invention for producing a concentrate, in particular an acidic liquid concentrate for preparing a dialysis solution, preferably a dialysis solution for hemodialysis.

The present invention additionally relates to a dialysis machine or a preparation unit for preparing a dialysis concentrate which is connected to a container according to the invention. In doing, so the connecting means of the container is connected to two fluid lines in the dialysis machine and/or in the preparation unit for dialysis solutions.

A fluid, preferably water, can be introduced into the container through a fluid line. In a special embodiment, a fluid, preferably water, and a gas, preferably air, can be introduced into the container at the same time.

If the fluid concentrate is present in a suitable concentration in the container, then a supporting element in the form of an air cushion can be filled by introducing a gas, so that this assumes a largely fixed shape, thereby stabilizing the flexible container.

The dialysis machine may have devices by means of which the fluid, preferably water and/or a gas, preferably air can be removed from the container.

Valves that can be used to establish a certain pressure in the container may also be present in the fluid line of the dialysis machine, which is connected to the venting means of the container. Then a pressure gauge may be provided in the vent line of the dialysis machine which is connected to the vent line of the container. In this way the valve may be closed until the air cushion has been filled. This can be tested by achieving a certain pressure level. The valve may be opened if additional gas, preferably air must then be introduced into the container for thorough mixing of the concentrate. There is no excessive pressure in the container. The pressure built up in the air cushion is retained if the air cushion is connected to the container compartment for the concentrate via a non-return valve.

Furthermore, the dialysis machine or the preparation unit may have at least one control unit or regulating unit, which is designed so that it controls or regulates the supply of fluid, preferably water and/or gas, preferably air into the container and/or the removal of gas, preferably air and/or a fluid concentrate from the container.

In addition, this control and regulating unit may be configured so that it uses signals of the pressure gauge to control the closing and opening of the valve in the vent line of the dialysis machine.

The present invention also relates to a method for providing a stable container for concentrates for dialysis, said container being connected to a dialysis machine or a preparation unit for preparing dialysis concentrates. When a fluid, preferably water and/or a gas, preferably air, is supplied, a supporting function develops due to the supporting elements integrated into the container. An air cushion can be filled by supplying a fluid, preferably water and/or supplying a gas, preferably air, which then stabilizes the container.

One alternative possibility is that the increase in volume of the container caused by the addition of the fluid leads to widening of a mechanical supporting element that was previously folded, thereby stabilizing the container.

BRIEF DESCRIPTION OF THE DRAWINGS

Additional details and advantages of the invention are described in greater detail on the basis of the exemplary embodiments shown in the drawings, which show.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
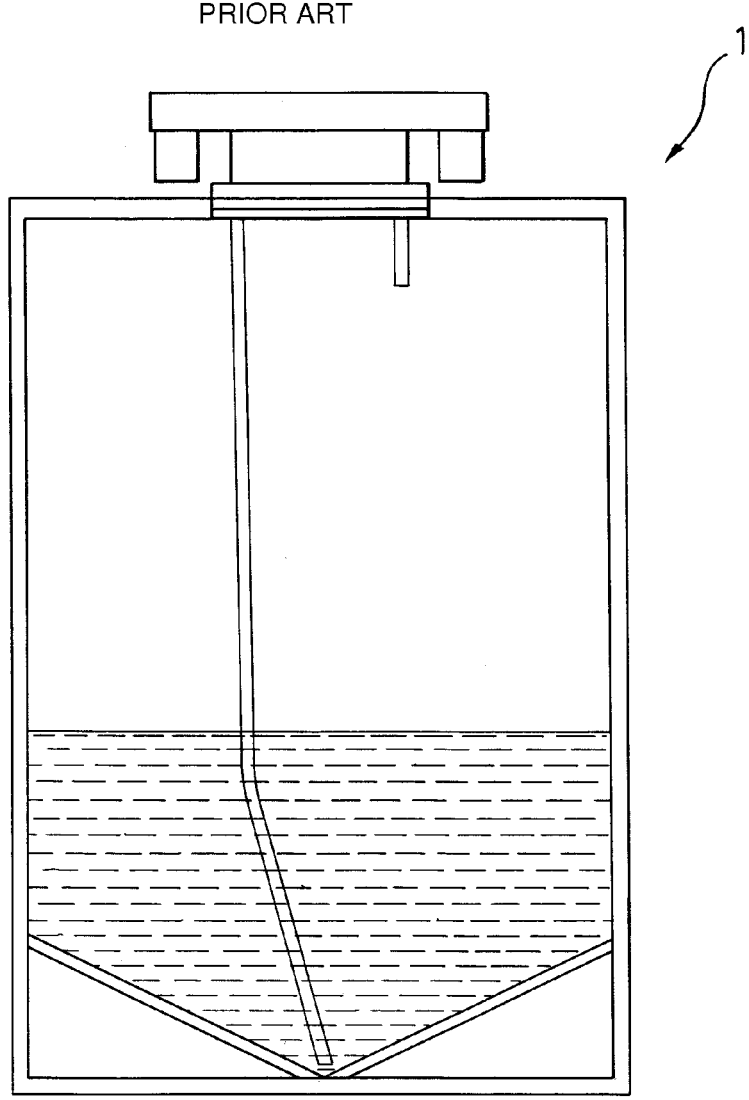
FIG. 1: Schematic view of a container for concentrates according to the prior art.

FIG. 1 illustrates a container 1 according to the prior art.

Figure 2:
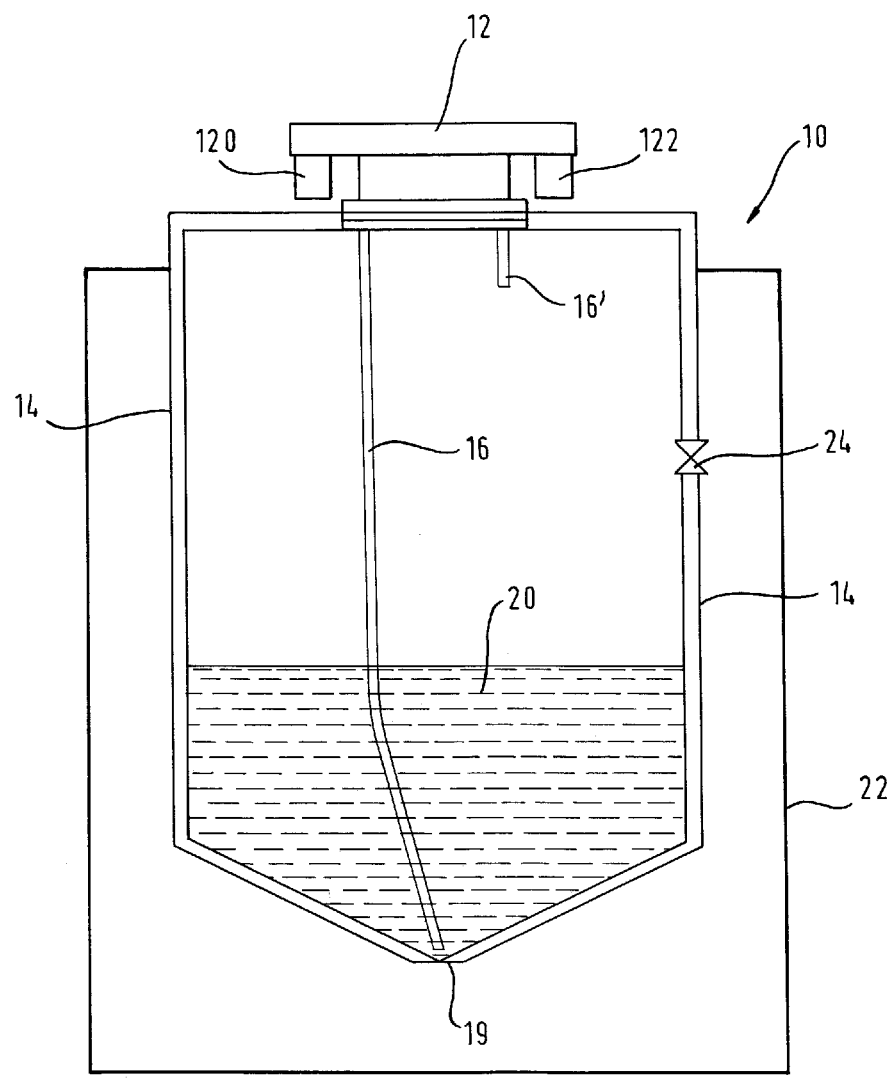
FIG. 2: Schematic front view of a container according to the invention with the filled air cushion, partially filled with liquid concentrate.

FIG. 2 shows a container 10 according to the invention, which is designed as an inner bag 14 having flexible walls made of plastic. The walls are welded together on the bottom side of the container, forming a valley-shaped area 19. A connecting means 12 provided on the top side of the container has a first connector 120 which is directed outward and a second connector 122 which is also directed outward and with which the container 10 is mounted on the dialysis machine. The first connector 120 forms the fluid connection to the insertion means through which the fluid and/or gas is introduced into the container 10. The insertion means protrudes into the lower valley-shaped area 19 of the container 10, which is partially filled with concentrate 20. This design optimizes the dissolving of the dry concentrate in the preparation of a liquid concentrate by a method such as that described in DE 10 2011 106 248.7. The second connector 122 forms the fluid connection to the vent means 16' through which gas that is introduced into the container during the execution of the method described in DE 10 2011 106 248.7, for example, can be expelled from the container into the dialysis machine. The inner bag 14 is largely surrounded by an air-filled outer bag 22. A non-return valve 24 connecting the inner bag 14 to the outer bag 22 is provided in the wall 14. The outer bag 22 can thus be filled with gas, which is sent from the dialysis machine into the inner bag through the connector 120 and the insertion means 16. However, the gas can also be introduced into the container 10 from the outside through a valve (not shown) mounted in the outer bag. The outer bag 22 is shown here in the filled state. Due to its rigid shape, it supports the fluid-filled inner bag 14. The outer bag 22 has a straight shape on the bottom, so that the container 10 is self-supporting.

Figure 3:
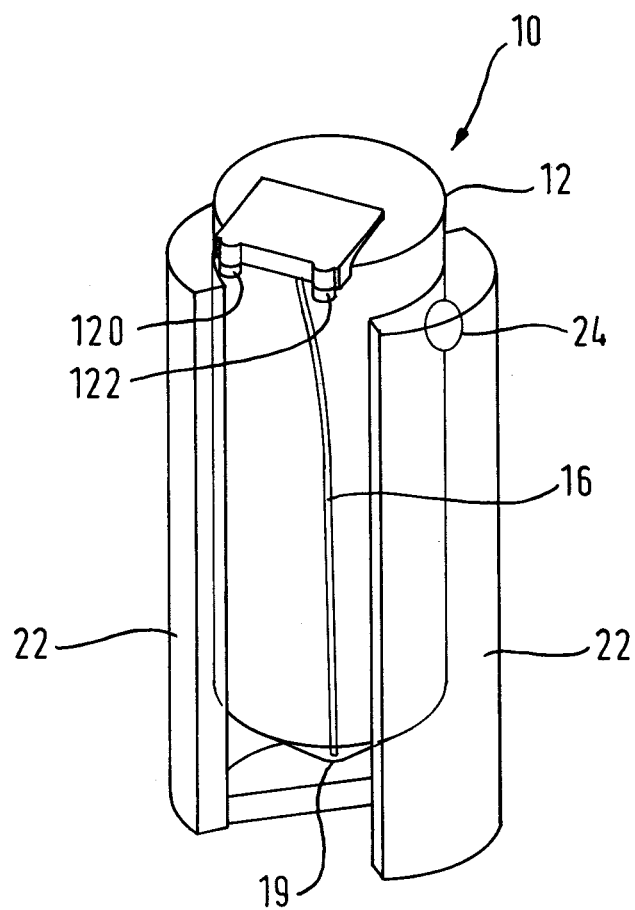
FIG. 3: Perspective rear view of a container according to the invention with a filled air cushion.

FIG. 3 shows the supporting function of the air cushion in the perspective diagram of the container 10.

Figure 4:
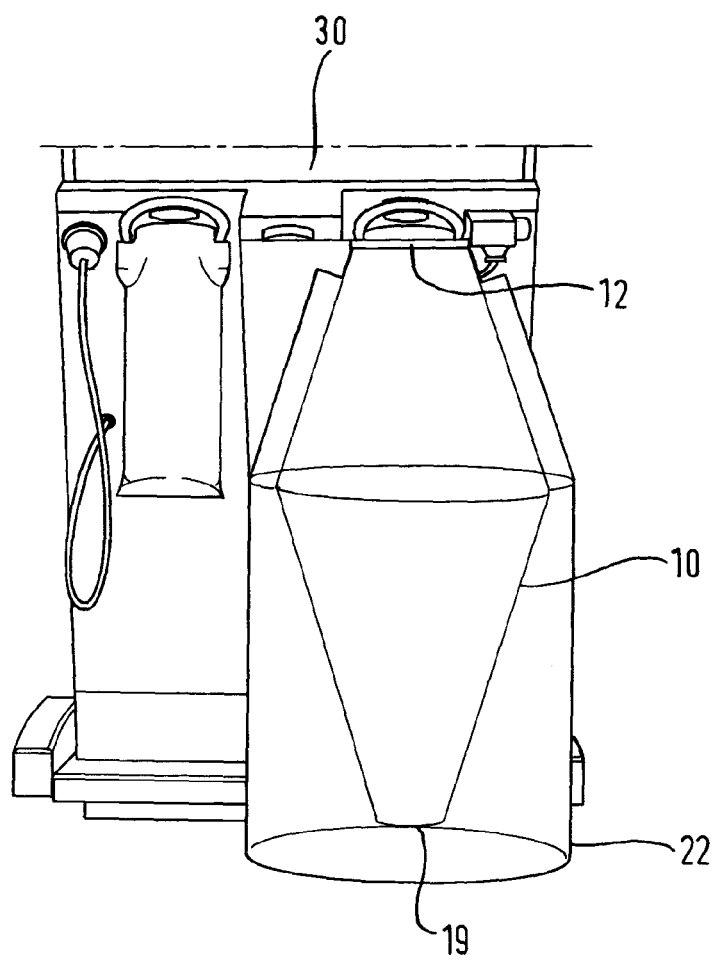
FIG. 4: Schematic front view of a container according to the invention mounted on a dialysis machine.

FIG. 4 shows the container 10 of acid concentrate connected to a dialysis machine 30. Since the container 10 stands on the bottom, there is no tensile load due to the weight of the container on the connection of the dialysis machine 30.

Figure 5:
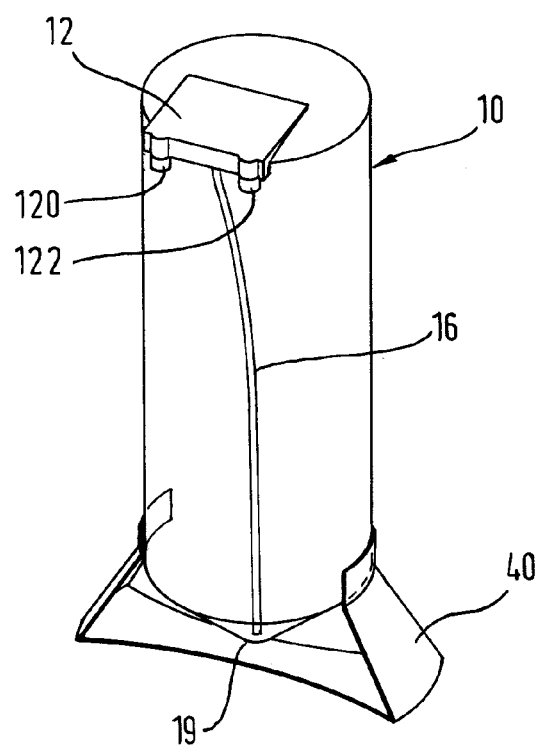
FIG. 5: Perspective view of a container according to the invention with an unfolded supporting element.

FIG. 5 shows a container 10 according to the invention, stabilized by a foot 40 that unfolds during the filling operation.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A container for containing a concentrate suitable for preparing a dialysis solution, said container comprising:
   a connecting element situated at a top portion of the container by which the container is connectable to a dialysis machine or to a preparation unit for a liquid concentrate;
   an inner container, and an air cushion structure that exerts a supporting function to the container only when air is supplied thereto, a bottom of the air cushion structure being situated at a bottom portion of the container;
   an insertion element in communication with the connecting element, the insertion element being configured to communicate the air to the container and a liquid concentrate from the container; and
   a non-return valve that provides for communication of the air between the inner container and the air cushion structure,
   the container being self-standing in a substantially vertically upright orientation.

2. The container according to claim 1, wherein the concentrate is a dry concentrate.

3. The container according to claim 1, further comprising a vent.

4. The container according to claim 1, wherein the concentrate is an acidic liquid concentrate associated with preparing the at least one dialysis solution for a hemodialysis.

5. A dialysis machine or a preparation unit for preparing a dialysis concentrate, wherein the dialysis machine or the preparation unit is connected to a container according to claim 1.

6. The dialysis machine or preparation unit according to claim 5, wherein the dialysis machine or the preparation unit is configured to supply the air to the container.

7. The dialysis machine or preparation unit according to claim 5, further comprising at least one control or regulating unit that controls or regulates at least one of the supply of the air to and a removal of the air from the container.

8. The container according to claim 1, wherein the inner container is configured to hold the concentrate, and wherein the air cushion structure surrounds the concentrate-containing inner container.

9. The container according to claim 1, wherein the insertion element communicates a liquid and the air to the container.

10. The container according to claim 9, wherein the liquid is water.

* * * * *